(12) United States Patent
Anandhakrishnan (10) Patent No.: US 10,393,394 B2
(45) Date of Patent: Aug. 27, 2019

(54) SYSTEM, METHOD AND DEVICE TO RECORD PERSONAL ENVIRONMENT, ENABLE PREFERRED PERSONAL INDOOR ENVIRONMENT ENVELOPE AND RAISE ALERTS FOR DEVIATION THEREOF

(71) Applicant: Vaidyanathan Anandhakrishnan, Bangalore (IN)

(72) Inventor: Vaidyanathan Anandhakrishnan, Bangalore (IN)

(*) Notice: Subject to any disclaimer, the term of this patent is extended or adjusted under 35 U.S.C. 154(b) by 563 days.

(21) Appl. No.: 14/130,680

(22) PCT Filed: Nov. 21, 2013

(86) PCT No.: PCT/IB2013/060295
§ 371 (c)(1),
(2) Date: Jan. 3, 2014

(87) PCT Pub. No.: WO2015/044724
PCT Pub. Date: Apr. 2, 2015

(65) Prior Publication Data
US 2015/0088786 A1 Mar. 26, 2015

(30) Foreign Application Priority Data
Sep. 25, 2013 (IN) .......................... 4346/CHE/2013

(51) Int. Cl.
*F24F 11/30* (2018.01)
*G16H 50/20* (2018.01)
*G16H 50/80* (2018.01)
*F24F 110/00* (2018.01)
*G16H 50/30* (2018.01)

(52) U.S. Cl.
CPC ............ *F24F 11/30* (2018.01); *G16H 50/80* (2018.01); *F24F 2110/00* (2018.01); *G16H 50/20* (2018.01); *G16H 50/30* (2018.01)

(58) Field of Classification Search
None
See application file for complete search history.

(56) References Cited

U.S. PATENT DOCUMENTS 7,574,769 B1 * 8/2009 Nemeth ............... B60S 1/3404
15/250.003
7,594,889 B2 9/2009 St. Ores
(Continued)

FOREIGN PATENT DOCUMENTS

WO 2012023136 2/2012

OTHER PUBLICATIONS

Krause, Andreas, Asim Smailagic, and Daniel P. Siewiorek. "Context-aware mobile computing: Learning context-dependent personal preferences from a wearable sensor array." Mobile Computing, IEEE Transactions on 5.2 (2006): 113-127.*
(Continued)

*Primary Examiner* — Scott A. Waldron
*Assistant Examiner* — Kevin W Figueroa
(74) *Attorney, Agent, or Firm* — J. Peter Paredes; Rosenbaum IP, P.C.

(57) ABSTRACT

The system has number of environmental sensors to sense various environmental parameters of the personal environment envelope surrounding the individual and multiple biological sensors to sense biological and physiological condition of the individual. The system includes a personal environment envelop setting module to define preferred settings based on input from the individual. The system has a processing module to process the environmental parameters sensed by the sensors and the preferred settings to generate alerts. The processing module, also receives information from other sources and is capable of dynamically compute recommendations, map these with the preferences of the individual for enabling the preferred conditions. The
(Continued)

system also has a server module configured to receive, store, analyze and machine learn from data of the plurality of environmental parameters sensed by the plurality of sensors and the preferred settings along with ambient environmental data from plurality of persons for epidemiology study.

17 Claims, 6 Drawing Sheets

(56) References Cited

U.S. PATENT DOCUMENTS

| | | |
|---|---|---|
| 8,807,131 B1 | 8/2014 | Tunnell |
| 2006/0173580 A1 | 8/2006 | Desrochers |
| 2008/0281472 A1* | 11/2008 | Podgorny ............ F24F 11/0009 700/276 |
| 2009/0194104 A1 | 8/2009 | VanSickle |
| 2012/0041604 A1* | 2/2012 | Isaksson ................ E21F 1/02 700/277 |
| 2014/0222210 A1* | 8/2014 | Agarwal ................ G05B 15/02 700/275 |

OTHER PUBLICATIONS

Satish, U. et al. "Is CO2 an Indoor Pollutant? Direct Effects of Low-to-Moderate CO2 Concentrations on Human Decision-Making Performance," Environmental Health Perspectives, vol. 120, No. 12, Dec. 2012, pp. 1671-1677.

* cited by examiner

SYSTEM, METHOD AND DEVICE TO RECORD PERSONAL ENVIRONMENT, ENABLE PREFERRED PERSONAL INDOOR ENVIRONMENT ENVELOPE AND RAISE ALERTS FOR DEVIATION THEREOF

PRIORITY CLAIM

The present application is a U.S. national stage application (under 35 USC §§ 371) of PCT international application PCT/IB2013/060295 having an international filing date 21 Nov. 2013, which claims priority from Indian non-provisional application no 4346/CHE/2013 filed with the Indian Patent Office on 25 Sep. 2013.

TECHNICAL FIELD OF THE INVENTION

The present disclosure relates to an environmental tracking, monitoring and enable control of the personal environment, create alerts for deviations thereof. More particularly, the present disclosure relates to a system and method and device for recording and enabling alerts regarding personal environment, interface with other equipments to enable achieve preferred personal environment.

BACKGROUND OF THE INVENTION

Breathing is an involuntary act that keeps a person alive. The quality of air one breathes depends upon the place the person inhabits and the immediate surrounding around the person, whether outdoor or indoor.

Outdoor, ambient, environment pollution is of importance to all, World Health Organization (WHO) estimates that the total number of persons impacted by COPD (Chronic Obstructive Pulmonary Disorder) is about 210 Mn. As per CDC (Centre for Disease control, USA), the incidence of COPD in USA is estimated at over 12 Mn. Apart from this it is estimated that about 25 Mn Americans (Adults & Children included) suffer from Asthma. These respiratory illnesses are predominantly caused by the quality of inhaled air. From public health perspective environmental pollution has been extremely well researched. Governments, both at Federal and at State level have been drawing new and more demanding standards to curb increasing pollution. CDC considers air pollution is a leading environmental threat to human health. Particles in the air such as dust, dirt, soot, and smoke are one kind of air pollution that is known to cause health problems. Very fine particles less than 2.5 micro meters are known as particulate matter or $PM_{2.5}$. These are small enough to be inhaled deep into the lungs. Thus causing serious illnesses and death. The chemical pollutants would be caused by COx (Carbon Di-Oxide, Carbon Monoxide etc.) NOx, (Nitric Oxide, Nitrous oxide etc.,) SOx (Sulphur dioxide etc.), Volatile Organic Compounds (VOC), Radon and other such impurities. The biological impurities could be presence of columns of bacteria or virus or other micro organisms that could influence the quality of air. In effect air pollution could be due to physical impurities, chemical impurities or biological factors. Biological pollution is of a growing concern. In recent instances of growth of Bird Flu, Swine Flu and other mutant variations, the biological impurities caused by viruses such as H1N1, H7N9 have been reported.

As regards Indoor Environments advancement of technologies provided for controlled environment through various equipments collectively known as heating ventilation and air conditioning (HVAC) equipments such as air-conditioning devices that performed different functions such as cooling and heating of air, humidifying and dehumidifying air as required, enabling conditioned working and living environments while being indoor. Inadequate injection of fresh air into such conditioned indoors has created various illnesses and World Health Organization (WHO) in their studies categorized such phenomenon as 'Sick Building Syndrome'—SBS. The resultant poor 'Indoor Air Quality' called IAQ (Indoor Air Quality) has been a subject of serious discussion and debate in the industry and amongst people. As per US EPA (Environment protection agency) there are many sources of indoor air pollution in a home or office or any other building. IAQ along with other parameters such as the acoustic levels in the occupied space, lighting and other factors are called 'Indoor Environment Quality'—IEQ. A lot of equipments and gadgets are present in the market to enhance Indoor air quality as well as IEQ Health problems to human beings due to indoor air pollutants may show up after a single exposure or repeated exposures. These include irritation of the eyes, nose, and throat, headaches, dizziness, nausea and fatigue. Such immediate problems are usually short-term and treatable. Sometimes the treatment is simply eliminating a person's exposure to the source of the pollution, if it can be identified. Certain immediate effects are similar to those from colds or other viral diseases such as nasal irritation, so it is often difficult to determine if the symptoms are a result of exposure to indoor air pollution. For this reason, it is important to pay attention to the time and place symptoms occur. If the symptoms fade or go away when a person is away from home, for example, an effort should be made to identify indoor air sources that may be possible causes. Some effects may be made worse by an inadequate supply of outdoor air or from the heating, cooling, or humidity conditions prevalent in the home. Other health effects may show up either years after exposure has occurred or only after long or repeated periods of exposure. These effects, which include some respiratory diseases, heart disease, and cancer, can be severely debilitating or fatal. It is prudent to try to improve the indoor air quality in your home or office even if symptoms are not noticeable.

The quality of air that one breathes continuously impacts one's health. This will vary depending upon the place the person in, the immediate surrounding environment i.e, the personal environment or personal surrounding around him. While a lot of research and effort has gone into Environmental pollution, as well as IAQ it needs to be noted that it is personal air quality (PAQ) or the air that one breathes would influence the person's health The impact of the quality of air would vary from an individual to an individual. Hence the need to measure, track and monitor the quality of air that the individual breathes Quite often $CO_2$ is taken as a proxy for the indoor pollution. Recent studies have increased the importance of understanding the $CO_2$ levels in the room. It is also known that for illnesses such as asthma the air that one breathes is of extreme relevance. It is known that high $CO_2$ levels as well as relative humidity of air influences the comfort for asthma patients. Over time and experience a patient learns on the environment where the person is comfortable and would prefer such environment as compared to another environment that the person knows as discomforting. It is also reported that the absenteeism in schools is because of the quality of the indoor air.

Most of the existing HVAC equipment has static settings based on specific set points such as temperature, relative humidity. Some of the advanced equipments have a set of programmed set points or patterns based on which these equipments operate. In a few of the newer control devices, the equipments learn based on the settings and patterns of usage specifically with regard to temperature. However none of these devices provide a dynamically variable preferred setting based on the persons' preferred setting that correlates to his health. For an example if an asthmatic person would prefer an air envelope of say Temperature of 23 to 27 deg. C. with a relative humidity of 50% to 65% and a $CO_2$ level of lesser than 600 ppm in the room, the equipment in his house could be told to provide such environment as much as his office equipment or any other place that he would visit.

Epidemiology is the cornerstone of public health science and equips policy decisions by the Government agencies; the study helps identifying the risk factors for a disease and helps in preventive steps for occurrence of such disease/illness. Every person keeps a record of the illness to enable better medical history and treatment for longevity and quality of life. In these days of advanced technology, medical records and genetic history/genealogy analysis is undertaken to arrive at causes for the illness or as important factors for the specific treatment that would be provided to the person. While such level of information is gathered, seldom does a person have a record of the air that he breathed There are many existing patent applications which talk about the preferred environment for a building or for a hospital or the like. US2006173580A1 discloses an air quality monitoring systems and methods. The indoor air quality system relates to an air monitoring system that is portable and the parameters to be monitored can be customizable for a specific structure, such as a building or a home and communicates the monitored parameter to the user through internet.

Another PCT application WO2012023136A1 also discloses a device, system and method for personal health monitoring based on multitude-points environmental data. Here, the system or device gets various environmental data raise alerts, but the application does not disclose about enabling the user for adaptive comfort setting based on these data.

None of the existing devices gives alerts when there is a deviation in the preferred settings of the user. There are many devices available which are capable of giving weather conditions such as NETATMO™ and other gadgets that could enable the user to have specific settings, such as those offered by HONEYWELL™. But none of these products or patents discloses a system or method or device for recording and enabling alerts regarding deviations from the preferred personal environment or which helps in setting adaptive comfort for the air conditioner and a cost effective and easy to use. None of these gadgets provide data at the back end for collection of data pertaining to preferred settings of an individual.

There are a few community initiatives to capture the air quality and consolidate the data to map the quality of air in a community. Citisense was one such initiative by University of California, San Diego wherein they created a wearable, low power, air quality and environmental monitoring sensor node that can be used in mobile and stationary settings. The sensor node includes a microcontroller for local data analysis and a Bluetooth transceiver to communicate with a smartphone.

Similarly another project 'Common Sense Community' was an initiative by University of California, Berkeley to get novice users to capture data around them with different sensing technologies. While both Citisense/Common sense were initiatives to demonstrate possibilities of integrating technologies, they have not been converted into a device that can capture micro personal environment, namely the inhaled air quality of an individual and to enable preferred settings or enable interaction with other equipments.

Thus there is a need for a system, method and device that would capture the micro personal environment/personal cloud of the air that the individual would seek, inhale, learn from the preferred settings through an user interface the personal preferences, alert in event of deviations from the preferred settings, provide data to the backend server that could through a period of time of accumulated data provide valuable health insights to the person as well as act as the database of several individuals health records to enable health specialists, epidemiologists to study and analyze such data to guide policy formulations.

SUMMARY OF THE INVENTION

According to an embodiment, the invention discloses a system for recording personal environment envelope of an individual. The system includes a sensor module which has at least one of a plurality of environmental sensors configured to sense a plurality of environmental parameters of the personal environment envelope surrounding the individual and a plurality of biological sensors to sense a plurality of biological and physiological condition of the individual. The system also includes a personal environment envelop setting module configured to define preferred settings based on input from the individual. The personal environment envelop setting module is also configured to machine learn individual's preference of the personal environmental envelope and to automatically generate the preferred settings for the individual based on the learning. The system also has a processing module configured to process the plurality of environmental parameters sensed by the plurality of sensors and the preferred settings to generate one or more alerts. The processing module through the inputs received from external information sources and based on the ambient environment compute dynamically the recommendations, map these with the preferences of the individual for communicating to other devices that enable achieve the preferred conditions. The alert indicates a deviation of at least one environmental parameter from a corresponding preferred setting. The system also has a server module configured to receive, store, analyze and machine learn from data of the plurality of environmental parameters sensed by the plurality of sensors from the sensor module and the preferred settings along with ambient environmental data from plurality of persons for epidemiology study.

The system also includes a communication module configured to communicate alerts with plurality of devices. The sensor module is further configured to perform signal conditioning for the plurality of sensor. The processing module is also configured to collect data from plurality of sensors regarding ambient environmental conditions with reference to the geographical location of the individual. The processing module also collects data from plurality of external sources regarding ambient environmental conditions with reference to the geographical location of the individual and the personal environmental envelope.

According to an embodiment, the system further includes a server module configured to receive data from the communication module regarding the plurality of environmental parameters sensed by the plurality of sensors and the preferred settings from plurality of persons for performing epidemiology study my mapping preferences with reasons or causes or ailments with the help of infographics. When the individual moves from a first personal environment envelope to a second personal environment envelope, the personal environment envelop setting module is also configured to generate adaptive comfort settings for the individual present in the second personal environment envelope based on environmental parameters of the first personal environment envelope and the corresponding ambient or outdoor conditions.

According to an embodiment, the invention discloses a method for recording personal environment and to enable preferred personal indoor environment. The method includes step of collecting data regarding environmental parameters of the personal environment envelope surrounding an individual and biological and physiological conditions of the individual from a plurality of sensors. The method also includes the step of receiving input from the individual regarding preferred personal environment setting, and processing the collected data and received input to identify any variations in the preferred personal environment settings to generate one or more alerts, wherein the alert indicates a deviation of at least one environmental parameter from a corresponding preferred setting. The method also includes step of communicating the alerts with plurality of user devices. When the individual moves from a first personal environment envelope to a second personal environment envelope the method further includes step of generating an adaptive comfort setting for the individual. The method also includes step of recording the various inputs received from the individual and from the sensors.

According to an embodiment, the invention discloses a device for recording personal environment and to enable preferred personal indoor environment. The device includes a processor, a plurality of sensors for sensing a plurality of environmental parameters of the personal environment envelope surrounding the individual, an air flow enabling module to allow the air to circulate inside the device, to accurately and dynamically capture the properties of air surrounding the individual as the device would be close to the body of the individual a personal environment envelop setting module configured to define preferred settings based on input from the individual through an user interface. The personal environment envelop setting module is also configured to machine learn individual's preference of the personal environmental envelope and to automatically generate the preferred settings for the individual based on the learning. The device also has a processing module configured to collect data from plurality of sensors regarding ambient environmental conditions with reference to the geographical location of the individual, to collect data from plurality of external sources regarding ambient environmental conditions with reference to the geographical location of the individual and the personal environmental envelope and to dynamically process the preferred personal environment data vis-à-vis the ambient environmental conditions. The processing module also process the plurality of environmental parameters sensed by the plurality of sensors and the preferred settings to generate one or more alerts, wherein the alert indicates a deviation of at least one environmental parameter from a corresponding preferred setting. The device has a display unit to present the plurality of environmental parameters and alerts generated by the processing module and a power supply module configured to supply power to the device.

According to an embodiment of the invention, weather information available from plurality of sources such as Government, Community or individuals by way weather warnings such as heat wave or dust storms or storms, air quality index (AQI), pollen levels or index, would be collected through application program interface (API), used for the respective geographical area of the user of the device to provide inputs regarding the ambient environment to enable dynamically compute the preferred settings.

The device also has a communication module configured to receive and transmit data between various modules and to communicate alerts and interface with plurality of user devices. The personal environment envelop setting module of the device is configured to interact and interface with various environment setting equipments to achieve the preferred setting for the individual. The air flow enabling module employs at least one of first louvers for air to flow into the device and second louvers for air to move out or a mini fan to enable air circulation. The air flow enabling module has one or more of a spring loaded disc that rotates to create turbulence, a heater to create a thermal gradient or a passage to move air through a Venturi effect. The device has a self cleaning mechanism for plurality of components of the device, to remove the fine dust that might have deposited inside the device. The self cleaning mechanism is a spring loaded cleaning system to clean reflective mirrors inside the device. The device also has a means for wearing the device on at least one of a body, apparel or an accessory. The power supply module has at least one of a USB port to get the device charged, a rechargeable battery, a solar cell or a wireless charging mode. The device further has one or more of a haptic, buzzer or light to enable alert.

According to an embodiment the sensors of the device are integrated in a wearable material on which the device is housed through a clip on facility.

According to another embodiment, the sensors integrated in the wearable material would communicate and interface with the device.

Thus system, method and device disclosed would capture the personal environment of the air that the individual would seek, learn from the preferred settings the personal preferences, alert in event of deviations from the preferred settings, provide data to the backend that could through a period of time of accumulated data provide valuable health insights to the person as well as act as the database of several individuals health records to enable epidemiologists to study, analyze such data to guide policy formulations.

BRIEF DESCRIPTION OF THE DRAWINGS

The foregoing and other features of embodiments will become more apparent from the following detailed description of embodiments when read in conjunction with the accompanying drawings. Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention. Thus, in the interest of clarity and conciseness, the drawings are generalized in form, wherein.

DETAILED DESCRIPTION OF THE INVENTION

In the following detailed description, reference is made to the accompanying drawings that form a part hereof, and in which is shown by way of illustration to specific embodiments that may be practiced. These embodiments are described in sufficient detail to enable a person skilled in the art to practice the invention, and it is to be understood that other embodiments may be utilized and that logical, mechanical, and other changes may be made within the scope of the embodiments. The following detailed description is, therefore, not be taken as limiting the scope of the invention, but instead the invention is to be defined by the appended claims.

The invention discloses a system, method and device to record personal environment envelope whether outdoor, indoor or travelling and to enable preferred personal indoor environment. The system has a number of sensors used to understand the personal environment envelop surrounding an individual. The system allows the individual to have preferred settings for the personal environment. The system also helps in keeping a check on the personal environment envelop and may alert the individual when there is a change in the personal environment from the preferred settings.

The personal environment envelope is basically the surrounding conditions that influence the quality of air on inhales that affect the health of the individual. The surrounding condition that envelops the person from the waist to the upper part of the body while a person is seated, standing, walking or sleeting is considered to facilitate the system. FIGS. 1A, 1B and 1C illustrate the personal environment envelop (101) that surround the individual. FIG. 1A illustrates the personal environment envelope (101) around the sleeping individual; where as FIG. 1B illustrates the personal environment envelope (101) around the individual who is standing. FIG. 1C illustrates the personal environment envelope (101) around the individual who is sitting on a chair.

Figure 1:
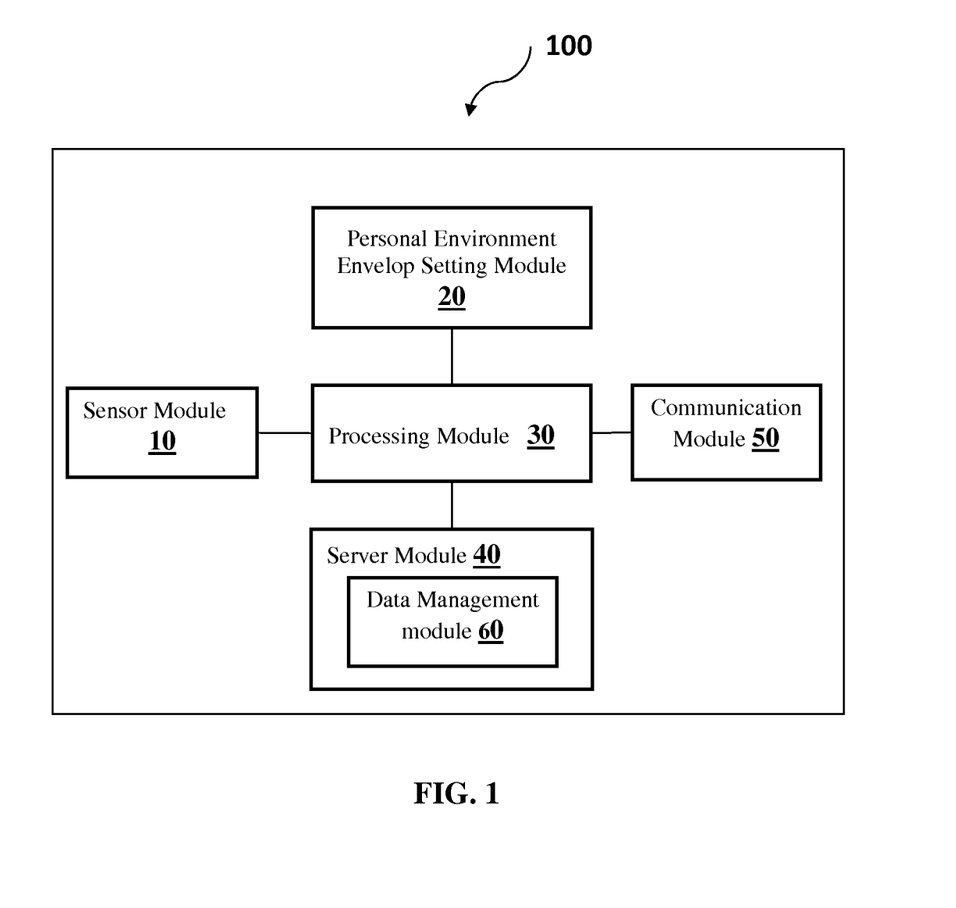
FIG. 1 illustrates the overall block diagram of the system in accordance with an embodiment of the invention.
Figure 1A:
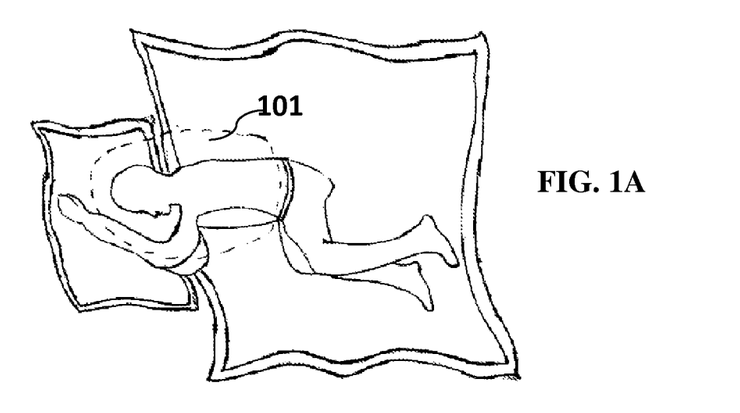
FIGS. 1A, 1B and 1C illustrate the personal environment envelope, personal surrounding of an individual in accordance with an embodiment of the invention.
Figure 1B:
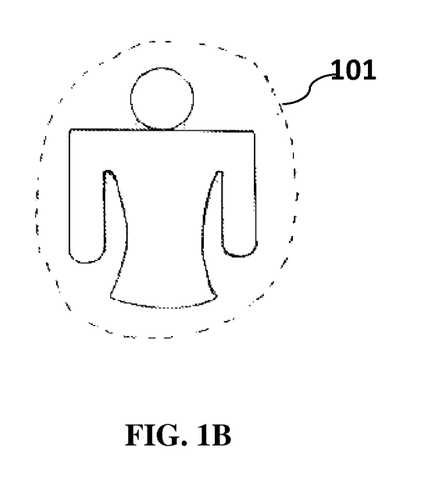
Figure 1C:
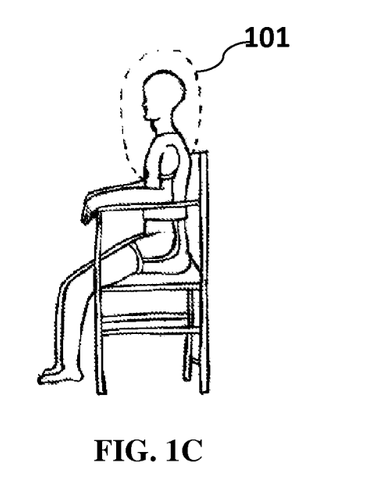

FIG. 1 illustrates the overall block diagram of the system in accordance with an embodiment of the invention. The system includes a sensor module (10) which has at least one of a plurality of environmental sensors configured to sense various environmental parameters of the personal environment envelope surrounding the individual and a number of biological sensors to sense a plurality of biological and physiological condition of the individual. In certain scenario the system may only have environmental sensors; in other scenarios it has the environmental sensors as well as the biological sensors. The environmental sensors described earlier includes sensors to collect environmental data such as $CO_x$ set of gases, $NO_x$ set of gases, SOx set of gases, volatile organic compounds, Radon, solid pollutants known as particulate matters of various sizes including but not restricted to dust, pollen, fine particles, Relative humidity (Rh), temperature, sound, light (harmful or beneficial), direction of flow of wind, location, direction in which the individual is facing or moving, altitude, barometric pressure, movement of the individual, alpha, beta and gamma wave etc. The biological sensors may be implanted in the individual's body or may be present on the body. The biological sensor includes sensors for identifying both the biological components as well as the physiological condition of the individual.

The system also has a personal environment envelop setting module (20) configured to define preferred settings based on the input from the individual through an user interface through a mobile, tablet or a phablet. The easy to read infographics, interactive signs such as like it, do not like it visuals will enable user friendly screen. The personal environment envelop setting module (20) is also configured to machine learn independently or with server module (40) individual's preference for the personal environmental envelope and to automatically generate the preferred settings for the individual based on the learning.

The system also has a processing module (30) to collect data from multiple numbers of environmental sensors regarding ambient environmental conditions with reference to a geographical location of the individual. The processing module (30) also collects data from plurality of external sources regarding ambient environmental conditions with reference to the geographical location of the individual and the personal environmental envelope. The processing module (30) further dynamically processes the preferred personal environment data in comparison with the ambient environmental conditions and process one or more of the environmental parameters sensed by the environmental sensors. The sensed biological and physiological condition of the individual along with the preferred settings of the individual is used to generate one or more alerts. The alert indicates a deviation of at least one environmental parameter from a corresponding preferred setting. The alert may even indicate a biological or physiological condition deviation. In certain scenario it may be deviation of both environmental parameter and biological or physiological condition.

In certain scenarios if the user is provided with an option to give the health conditions such as whether the user is asthmatic or he is has any particular allergy for pollens or any other environmental related allergy. So if the user gives such data through the personal environment envelop setting module (20) to the processing module (30) then the alerts are generated when there is a deviation from such standard values. Further, users are provided with a facility to change the setting according to their preference so that the alerts are generated accordingly. In an exemplary scenario when the user is an asthmatic patient. If the user suddenly feels uncomfortable by entering into a new environment or in the existing environment itself. Then the user is provided with an option to ask the system to provide data that may have caused problem. The system is intelligent to identify the parameters which have varied from the previous values and intimate the user. Thus it may be helpful for the asthmatic patients or others who is very sensitive to various environmental factors to identify the same and include those parameters also in their preferred settings. The various environmental data, biological and physiological data and the user inputs are being stored in the system in order to facilitate a continuous learning for the system depending on many factors such as age and health of the user with respect to the environmental condition. The personal environment envelops setting module (20) enables the users to configure their settings. The personal environment envelop setting module's (20) has the machine learning property which helps in identifying the preferred settings for the user.

According to an embodiment of the invention, the personal environment envelop setting module (20) is configured to interact and interface with various environment setting equipments to achieve the preferred setting for the individual. The various environment setting equipments include HVAC (heating ventilation and air conditioning), air conditioner, humidifier, air filtering equipments or actuators to enable flow of fresh air for diluting pollutants or any such equipments. The required communication protocols applicable is adhered to or followed through required software interfaces The system also has a server module (40) configured to receive, store, analyze and machine learn from data of the plurality of environmental parameters sensed by the plurality of sensors from the sensor module and the preferred settings along with ambient environmental data and plurality of inputs received from different gadgets and sources for different uses and applications from plurality of persons for individual as well as collective studies including epidemiology study. The data stored by the server module (40) enables data mining for understanding the correlation of various environmental parameters on the individuals' health. The big data stored in the server may be used for health and epidemiology studies.

The system further has a communication module (50) to receive and transmit data between various modules and to communicate alerts and interface with plurality of user devices. The alerts and notifications are generated based on the user input received as well as the various environmental factors such as $CO_x$ level, $NO_x$, $SO_x$ level, humidity, temperature or any such environmental factors which may affect the individual. The personal environment envelope setting module (20) utilizes the communication module (50) to communicate and interface with the environment setting equipments. The communication module (50) is configured to transmit the alerts or notifications to the various user devices which has been registered with the system to receive the alert. These user devices may be the mobile phone/tablets/phablets or any other device of the users who are authorized in receiving the individual's alert. The communication module (50) is further configured to transmit the user preferences from the personal environment envelop setting module (20) to the system so as to facilitate the setting of the preferred environment. The communication module (50) further enables the communication between the user device and the personal environment envelop setting module (20) also. In certain scenario the communication module (50) transmits the control signals for various indoor environment control equipments such as air conditioners or other HVAC (heating ventilation and air conditioning) systems or AC based on the personal environment envelop setting module's input through the processing module (30). In this manner the personal environment envelop setting module (20) interacts and interfaces with various environment setting equipments to achieve the preferred setting for the individual.

According to an embodiment of the invention, the system is also capable of identifying the proximity of the individual. The system with its algorithms is capable to identify whether the individual is within the envisaged defined range of personal environment envelop. If the user is not within the envisaged range the system alerts for variation from defined proximity through the communicating device, mobile or any other gadgets. This in turn ensures that the system collects only relevant data within the defined personal environment and not unrelated data.

According to another embodiment, when the individual moves from a first set of ambient conditions to a second set of ambient conditions then the personal environment envelop setting module (20) is configured to generate thermally adaptive comfort settings for the individual present in the second ambient conditions based on environmental parameters of the first personal environment envelope. Here the personal environment envelop setting module (20) interacts with the environment setting equipments to create a thermally adaptive comfort settings based on the first set of ambient conditions. Ambient condition is the condition that surrounds a person, so if the person is indoor then by ambient condition it represents the environment envelop that surrounds the individual within the indoor whereas if the person is in outdoor then the ambient condition is the environment envelop that surrounds the individual when he is outdoor. Adaptive comfort is based on the fact that people experience differently and adapt differently when they are coming in contact with a set of conditions from different conditions. The adaptability of the person depends on many factors such as their clothing's, physical activities, to the indoor conditions that exists and so on. For generating an adaptive comfort setting for the individual, the system consider the individuals thermal perception, behavior and other factors to calculate the thermal setting for the individual.

According to an embodiment, the sensor module (10) is further configured to perform signal conditioning for the plurality of sensors. The conditioning of signals helps in cleaning up the signal from the sensor.

In certain scenario the personal environment envelop setting module (20) exists in the user's personal device or user device which communicates to the system. It is also envisaged that the personal environment envelop setting module (20) may exist in a backend server which communicates to the system.

The alerts generated may include data to be sent to the individual or to any other user as an email or phone as sms or message according to the user decision. In some scenario alerts may be just a display of data or in the form of an alarm or haptics or a buzzer to warn the individual regarding any potential or real time change in the personal environment of the individual. The alerts may be in the form of LED/LCD display or a vibration or flash light or a projected display through devices such as a Pico Projector. In some embodiments individuals are also provided with an option to change the setting through their gadgets such as phone or tablet or smart phone or phablet or any other personal device such as a smart watch or bracelet. It is also possible to get the alert as a vibration in the above mentioned gadgets. In such cases the user's gadgets may store the sensor data and may send it to the remote location for storing. In certain scenario the alerts may be send to other users who are registered with the system to receive alerts regarding the variation of environmental parameters or physical or biological conditions of the individual.

The system may further has a server module (40) configured to receive data from the communication module regarding the plurality of environmental parameters as well the biological or physiological conditions of the individual sensed by the plurality of sensors and the preferred settings of the individual for performing epidemiology study. The sensors include both the environmental sensors and biological sensors. The server module further has a data management module (60) which helps in storing all the data acquired from the sensors, the data input by the users and other data relevant for the system such as the user's preferences, health condition. The server module (40) also has an analytical engine which performs analysis on the available data and enables the user to configure the necessary parameters as per his/her wish based on his health related conditions. Some sort of advisory may be provided to the user to help him/her to come to a conclusion related to the parameters sent from his/her device. The data management module (60) also helps in tracking the data of the user in terms of location, latitude and longitude, as well as altitude, ambient weather conditions including air properties, wind, sunshine, rain, the history of the air that the user breathed by way of all the air properties, physical, chemical or biological properties. Such accumulated data would provide valuable insights for the user to know the environment best suited to the person. History of such data would be valuable input for the health tracking system of the person. A data management module (60) of the server module (40) accumulates data of all the users, thus becoming a huge data base that can aid epidemiology which can serve public good at large. The individual record mapped with the illness along with the micro environment that the user experience would provide most useful data for analytics and data mining. The data analytics would be of immense value to the user, for the type of illness or treatment thereof, high level analysis for corporate and conglomerates, Government & public bodies for drafting policies pertaining to public health.

Figure 1D:
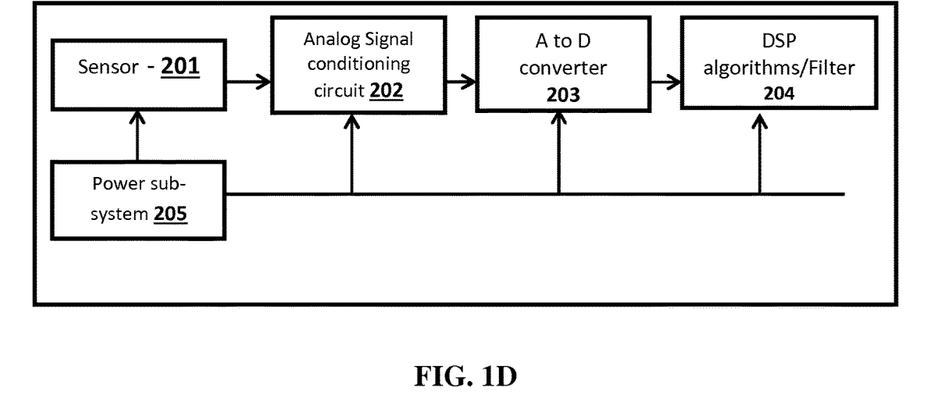
FIG. 1D illustrates the sensor module in accordance with an embodiment of the invention.

FIG. 1D illustrates the sensor module (10) in accordance with an embodiment of the invention. The sensor/s (201) which may be measuring various parameters such as temperature, relative humidity, CO2, CO, volatile organic compounds, radon etc. The analog signal conditioning circuitry (202) conditions the raw signal from the sensor/s (201) and provides the cleaned-up signal to the rest of the system. The analog to digital converter (203) converts the conditioned signal from the sensor/s (201) to the digital format so that any processing module (30) may process the data from the sensor/s (201). The digital filter/DSP algorithm based process run in a microprocessor or microcontroller which will further clean-up the signal from the sensor/s. The sensor module (10) further has a power sub-system (205) to regulate and supply as well control the power to the sensor/s (201). The power subsystem is (205) in turn programmed and controlled by the processing module (30) which enables the system to conserve power by providing power to components on requirement basis, sleep while not in use.

Figure 1E:
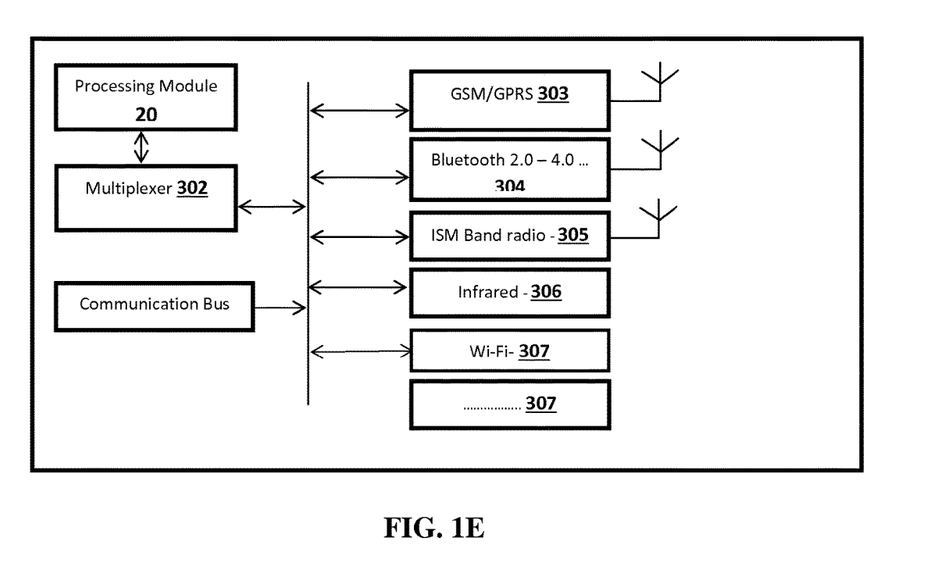
FIG. 1E illustrates the communication module in accordance with an embodiment of the invention.

FIG. 1E illustrates the communication module (50) in accordance with an embodiment of the invention. The multiplexer (302) gets controlled by the processing module (30) to send the data to a specific communication module such as GPRS/GSM module (303) or to multitude of module such as both to GPRS as well as to the ISM band radio (Zigbee etc.). The GSM/GPRS radio (303) or some such radio is used to communicate through cellular network. The Bluetooth based radio (304) is also available. The Bluetooth based radio (304) is used to communicate with phone/phablet/tablet/laptop app or personal devices such as smart watches, bracelets. The ISM band radio/s (305) is used to communicate with similar ISM band radios in the radio vicinity of the device. The infrared based module (306) is used to communicate with similar infrared based modules or gadgets. The Wi-fi module (307) may be activated while required for communicating through the network to other devices or systems as configured. The communication module is capable of incorporating with any future method of communication also.

Figure 1F:
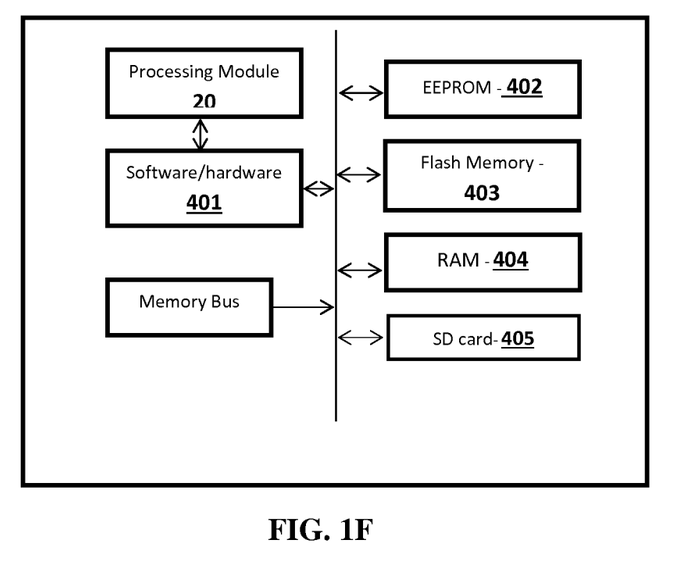
FIG. 1F illustrates the memory subsystem used by the data management module of the system in accordance with an embodiment of the invention.

FIG. 1F illustrates the memory subsystem used by the data management module (60) of the system in accordance with an embodiment of the invention. The hardware/software multiplexer (401) enables the processing module (30) to store data in either of RAM/EEPROM/FLASH etc. or multiple of the said technologies simultaneously. The EEPROM (402) stores data in a non-volatile manner. The FLASH memory (403) stores data in a non-volatile manner. The RAM memory module (404) helps in storing data for processing. The system may also has a memory storage facility such as a SD card (405).

Figure 1G:
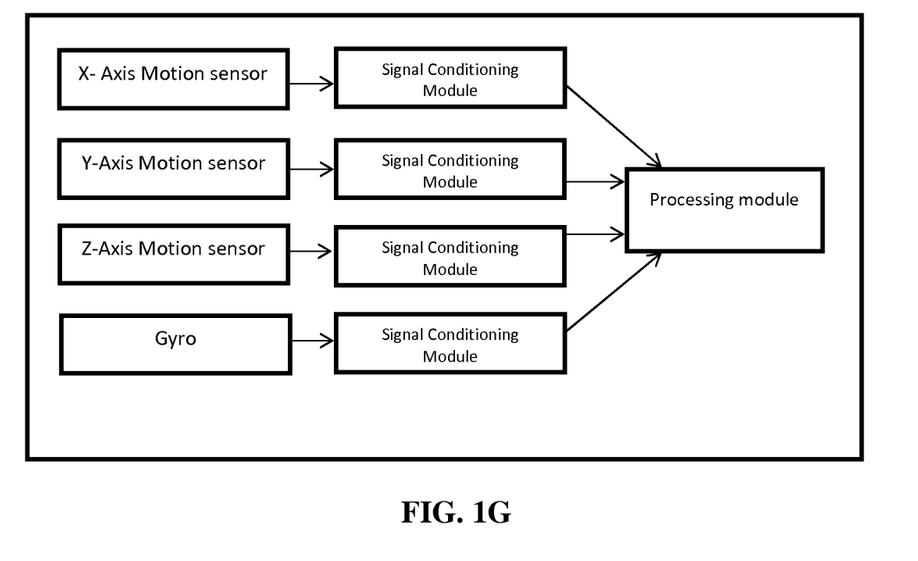
FIG. 1G illustrates the motion sub-system present in the sensor module for a motion sensor according to an embodiment of the invention.

FIG. 1G illustrates the motion sub-system present in the sensor module (10) for a motion sensor according to an embodiment of the invention. The motion sensing subsystem consists of three axes sensor/s which will sense motion of the individual in all the three axes. The output of the sensor/s will be passed through the signal conditioning circuits to eliminate any noise in the signal and the resultant signal will be passed to the processing module. In addition to the three axes motion sensor a gyro is also used to sense the motion of the individual and the output of the gyro is also processed in a similar way as described for the three axes motion sensor/s.

Figure 2:
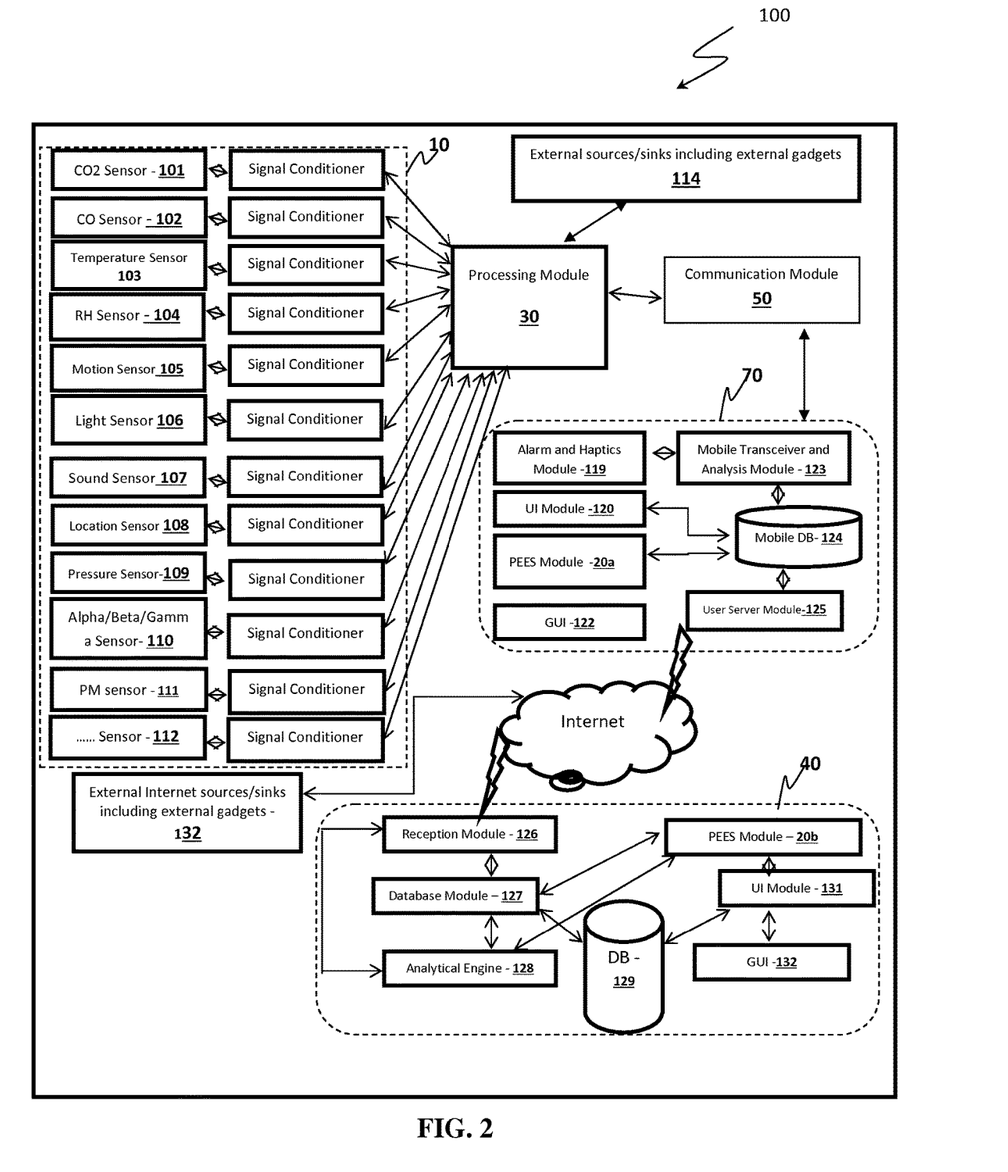
FIG. 2 illustrates the system according to an embodiment of the invention.

FIG. 2 illustrates the system according to an embodiment of the invention. The system (100) includes a sensor module (10), the sensor module includes a number of sensors to sense a variety of environmental parameters of the personal environment envelope surrounding the individual. For example the sensor module (10) has a $CO_2$ sensor (101), a CO sensor (102), a temperature sensor (103), a relative humidity sensor (104), motion sensor (105), light sensor (106), sound sensor (107), location sensor (108), pressure sensor (109), alpaha/beta/gamma sensor (110) and it may have any other sensors which is capable of sensing any of the environmental features related to the individual. The sensor module (10) further does signal conditioning in order to avoid any noise in the signal. The $CO_2$ (101) senses the $CO_2$ ppm in the surrounding air of the individual and the associated signal or data may be send to the signal condition circuitry for further processing. The CO sensor (102) measures the CO ppm in the surrounding air of the individual and the associated signal or data may be sending to the signal condition circuitry for further processing. The temperature sensor (103) measures the temperature in the surrounding air of the individual and the associated signal or data may be sent to the signal condition circuitry for further processing. The relative humidity (RH) sensor (104) measures the RH in percentage in the surrounding air of the individual and the associated signal or data may be sent to the signal condition circuitry for further processing. The motion sensor/s (105) measures the movement in three axes, namely X, Y and Z and also a Gyro measures the movement of the individual and the associated signal or data will be sent to the signal condition circuitry for further processing. The light sensor (106) measures the radiation in the visible and invisible spectrum and sends the associated data for further processing, where the output of the said processing will determine whether the said radiation is harmful to the individual or not based on agreed threshold values. The sound sensor (107) measures the sound in SPL in the surroundings of the individual and gets later processed and the output of the said processing determines whether the SPL is harmful to the individual or not based on agreed threshold values. The location sensor (108) measures the location of the individual. This may be based on technologies such as GPS/GSM based location technologies etc. The location sensor may also provide the altitude of the position of the user from mean sea level (MSL). The calculation of the wind direction can be either taken from wind direction sensor or from the web. The location of the individual can be calculated either from GPS or through GSM GPRS or through IP location etc. The pressure sensor (109) sends the data regarding the ambient/barometric pressure to the processing module (30) through a signal conditioning circuitry. Through the data from the pressure sensor, the system will determine the altitude of the location of the individual from the mean sea level (MSL). The alpha/beta/gamma wave sensor (110) senses the neurological activity of the individual and the data will be sent to the microprocessor. The microprocessor runs an algorithm/s to determine the mental state of the individual based on the waves generated by the individual. Particulate matter (PM) sensor (111) provides the details of count and distribution by size of particulate matter in microns from the air conveyed through it in the device to the micro processor The any other sensor (112) is to illustrate that the system is capable of incorporating any sensor to capture any other environmental data surrounding the individual or the biological or physiological condition of the individual and sends such data to the processing module. The processing module (30) includes the microprocessor for further processing. The processing module also receives data from the external source and sinks including external gadgets (114). The external sources might be other gadgets or sensors which might provide information to the system. The external sinks might be gadgets/appliances which might use the data generated by the device or the external sinks might be commanded based on certain thresholds by the device. Ambient/Outside air properties available through a plurality of sources such as external sources or other readily readable or processed to compute ambient air properties. Based on the ambient/outside air properties and computation of the indoor properties based on the data collected through the sensors through an algorithm, a reference set of parameters would be available for adaptive comfort setting of the air conditioning devices.

The processing module (30) is configured to receive and process the plurality of environmental parameters sensed by the plurality of sensors and the preferred settings from the personal environment envelop setting module (20) to generate one or more alerts. The alert indicates a deviation of at least one environmental parameter from a corresponding preferred setting. The processing module (30) utilizes various algorithms for calculating the air properties and also performs functions related to communication with the outside world. Calculation of air properties is an important functionality as it helps determine the local/personal or indoor condition with ambient conditions to the extent of activation of other devices such as air conditioners or humidifiers, or air filtering equipments or actuators to flow fresh air for diluting pollutants or any such operation. The data from these sensors are processed by intelligent microprocessors present in the processing module (30) and is sent to the user's personal devices such as smart phones, tablets, laptops etc. Also the data may be transmitted over the Internet to be stored in a remote server for analysis and future use. The processing module (30) with the help of communication module (50) gets access to a multitude of communication technologies to transmit data to the user's smart devices such as smart phones, tablets, phablets, smart watches, bracelets etc. as well as to the internet. According to an embodiment a buzzer or haptics/vibration actuator is coupled to the processing module to alert the user about any hazardous conditions based on thresholds which the user has created for himself/herself. The user may be any registered user to know the individual's data or alerts or the individual itself. According to an embodiment the output or the alert from the processing module (30) may be given through LED/LCD/projector. The output might be the parameters calculated by the device as well the alarms raised by the device. In another embodiment, the output may be through a single or a set of LED's or a multi-colored LED which will change its color based on certain inputs from the processing module. The color of the LED will indicate whether the environment around the user is preferred or safe or hazardous. The colors of the LED can be configured individually by the user According to an embodiment of the invention the memory subsystem of the server may present in the system itself. The memory sub-system comprises of RAM, non-volatile RAM, Flash memory, EEPROM etc. which are used for storing and retrieving data based on the availability of the communication medium as well for the purpose of proper computation of the algorithms. The communication module (50) gets data from the processing module (30) and transmits the information to the relevant locations. The communication module (50) uses numerous technologies such as GSM/GPRS, ISM band radios, Bluetooth versions, Wi-Fi, Infrared communication using various protocols etc. The communication module (50) is further capable of receiving and transmitting data between various modules of the system as well as to the user devices. The communication module (50) is capable of transmitting the sensor data from the sensor module to the user's computing devices such mobile phone/phablet/tablet application which in turn may be sent to the backend server. In certain scenario the processing module (30) may present in the user's computing devices. This is possible when the user's device has a software application which processes the data from the sensor module as well as personal environment setting module. The communication module (50) is also responsible for transmitting data to the server module (40) for storing and for future usage.

According to an embodiment of the invention the system (100) as shown in FIG. 2 further has a mobile or user device module (70) configured to receive data from the processing module (30) where the alarm and haptics module (119) in the user device raises the alarms or haptics (vibrations) in the user device. The user device includes any computing device which is capable of communicating with the system such as mobile phone, phablet, tablet or personal computer. The user device module (70) further has a user interface (UI) module (120) which controls the user interface. The user interface module (120) is tailored according to various operating systems which is available. The personal environment envelop setting module (PEES module) (20a) in the user device enables the user to configure his/her preferred settings such as $CO_2$/RH/Temperature/Particulate Matter levels etc. Those preferred settings are transferred to the device as well to the backend server through the communication module (50) so that the configuration set by the individual is available everywhere in the system. The GUI module (122) takes inputs from the user interface module and renders the graphics on the mobile phone/phablet/tablet based on the OS, screen size, resolution etc. The mobile transceiver and analysis module (123) is in the phone/phablet/tablet application analyses the data got from the processing module. The analysis is based on the configuration data set in the personal environment envelop setting module (20a). The user device module (70) further has a database module (124)

in the user device which stores the data from the processing module as well the confirmation data. This module stores historical data as well as data which were not sent over to the server module (40). The personal environment envelop setting module (20a) decides whether the data needs to be stored locally or not. The user server module (125) of the user device module (70) sends the data or receive the data as well the configuration information from or to the Internet. The server module (125) also responsible to pull or push data to the external gadgets and which might be designed to receive or send such data. The system is designed to receive information from other publically available information typically provided by Government agencies and other agencies on weather conditions, pollen levels and other such data which in turn would be received through an application programming interface (API) for use by the processing module (30) or server module (40) or by both of theses modules.

The server module (40) does the data management at the bank end side. The reception module (126) is a backend server which has a multithreaded application which receives data from millions of individuals. The plurality of data from a large set of individuals with various preferences based on their conditions, illness if any, chronic ailments if any, is most useful for predictive and prognostic advisory that will enable value added services as well as provide deep insights for public health and epidemiology. The database module (60a) receives the data from reception module (126) and stores the data in a RDBMS or such similar technology. The server module may be further capable of doing analytics on the data. Thus the stored data is used for analysis as well for generating info-graphics and also for future use. The analysis engine (128) in the server module (40) which analysis the data based on personal environment configuration settings and may send warnings or alerts to the user. The warnings might be in the form of SMS messages or missed calls or voice calls with configured messages.

There is a non-volatile database (129) based on RDBMS or some such technology which will be used to store the data as well the results from the analysis from an analytical engine (128). The non-volatile database (129) stores the user credentials for each user which is used by the user to enter the web-site. The server module (40) further has a personal environment envelop setting module (PEES module) (20b) to take inputs from the user, either from GUI (132) on the Internet or from the phone/phablet/tablet app through the GPRS or some such communication technology. The server module (40) uses algorithms for preferred health setting recommendations for different illnesses. The server module (40) also has provisions for incorporating algorithms based on contemporary findings on adaptive control for thermal comfort. The server module (40) would comprise of content generation through contemporary medical research and published data as well as releases from institutions such as FDA or EPA regarding recommended indoor environment, thus preferred personal cloud or micro environment settings for the user should there be any specific illness or ailment. With this as the reference, as the user records get updated, the preferred settings would correspond to the acclimatized micro environment/personal cloud. An algorithm to learn out of such acclimatized settings would in effect become the preferred personal settings. Thus server module along with the data management module accumulates data of all the users regarding preferred settings, ambient weather conditions and contemporary findings on thermal comfort, adaptive comfort settings and also provides data for personal settings. The individual record mapped with the illness along with the micro environment that the user experience would provide most useful data for analytics for epidemiology.

While several factors are important for health, lifestyle or occurrence of an illness, such collected data in conjunction with the ambient weather data, type of activities undertaken by the person would provide enormous insight for the Epidemiologists. This collection of data of the individual, the quality of air that he breathed along with the backend analysis of the data collected from several (millions) of individuals would well provide the background data for Epidemiologists to analyze the data that will help formulate health policies.

Figure 3:
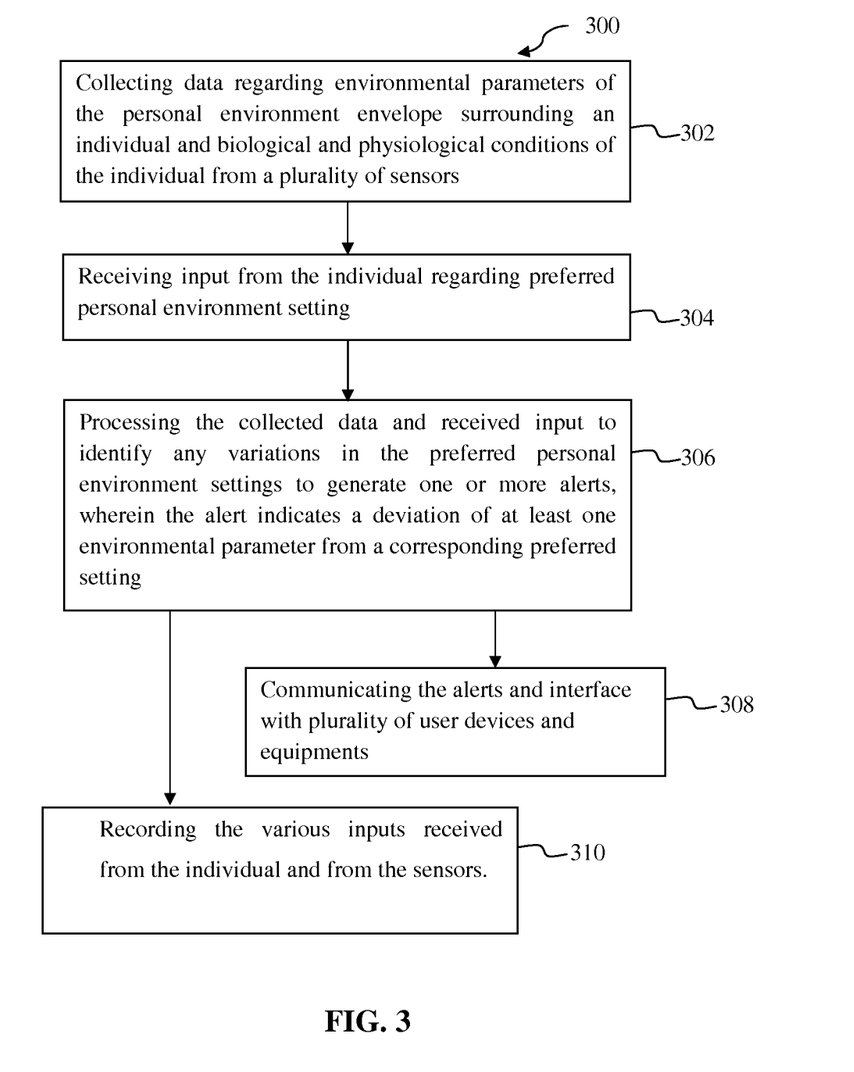
FIG. 3 illustrates the flow chart of the method for recording personal environment and to enable preferred personal indoor environment in accordance with an embodiment of the invention

According to an embodiment, the invention discloses method for recording personal environment and to enable preferred personal indoor environment. FIG. 3 illustrates the flow of the method. The method includes step (302) of collecting data regarding environmental parameters of the personal environment envelope surrounding an individual and biological and physiological conditions of the individual from a plurality of sensors. The plurality of sensors includes both the environmental sensors and the biological sensors. The method also includes step (304) of receiving input from the individual regarding preferred personal environment setting and step (306) of processing the collected data and received input to identify any variations in the preferred personal environment settings to generate one or more alerts, wherein the alert indicates a deviation of at least one environmental parameter from a corresponding preferred setting. The method also includes step (308) of communicating the alerts with plurality of devices. The method also has a step in which when the individual moves from a first set of ambient conditions to a second set of ambient conditions, wherein the personal environment envelop setting module is further comprises step of generating thermally adaptive comfort settings for the individual present in the second ambient conditions based on environmental parameters of the first personal environment envelope. The method further has a step (310) of recording the various inputs received from the individual and from the sensors in the backend. The recorded data is used for the epidemiology.

According to another embodiment, the invention further discloses a device for recording personal environment and to enable preferred personal indoor environment. The device includes a processor, a plurality of sensors for sensing a plurality of environmental parameters of the personal environment envelope surrounding the individual and an air flow enabling module to allow the ambient air to circulate inside the device. The device also has a personal environment envelop setting module configured to define preferred settings based on input from the individual, to machine learn individual's preference of the personal environmental envelope and to automatically generate the preferred settings for the individual based on the learning. The device also has a processing module configured to collect data from plurality of sensors regarding ambient environmental conditions with reference to the geographical location of the individual and to collect data from plurality of external sources regarding ambient environmental conditions with reference to the geographical location of the individual and the personal environmental envelope. The processing module dynamically process the preferred personal environment data vis-á-vis the ambient environmental conditions. The processing module also processes the plurality of environmental parameters sensed by the plurality of sensors and the preferred settings to generate one or more alerts. The alert indicates a deviation of at least one environmental parameter from a corresponding preferred setting. The device further has a display unit to present the plurality of environmental parameters and alerts generated by the processing module and a power supply module configured to supply power to the device. The device may also has a memory storage facility such as a SD card.

The device further has a communication module configured to receive and transmit data between various modules and to communicate alerts and interface with plurality of user devices such as mobile phone or tablet or any other such devices of the users who are registered to get the alerts.

According to an embodiment, the personal environment envelop setting module of the device is configured to interact and interface with various environment setting equipments to achieve the preferred setting for the individual. With this feature, the device helps the user to achieve a comfort setting by interacting with the various HVAC (heating ventilation and air conditioning) devices or air conditioning devices.

The air flow enabling module employs one or more of first louvers for air to flow into the device and a second louver for air to move out or a mini fan to enable air circulation. As a wearable device close to the body it would be subjected to the swings, sways and motions of the individuals which provides kinetic energy that could be used to move air within the device as also create increased velocity for air to move through the device. The air flow enabling module is designed in such a manner so as to ensure air flow and to have effective dynamic movement of air within the device through any design feature but not restricted to designs such as a spring loaded disc that rotates to create turbulence, a heater to create a thermal gradient or a passages to move air through a Venturi effect.

According to an embodiment of the invention, when the individual moves from a first personal environment envelope to a second personal environment envelope, the personal environment envelop setting module is configured to generate adaptive comfort settings for the individual present in the second personal environment envelope based on environmental parameters of the first personal environment envelope.

According to an embodiment of the invention, the device has a means that allows the individual to wear the device on at least one of a body, apparel or accessories. The means for wearing includes a clip on facility that allows the user to wear the device on their belt or using a wrist band and clipping the device on to the wrist band.

According to an embodiment of the invention the device may integrate data from sensors incorporated in a fabric that may be worn by the individual or it may be a belt or a wrist band or a head band or any other form that may be worn by the individual. Thus the device may be a wearable device.

According to an embodiment of the invention, the device has a self cleaning mechanism of many of the components of the device. The self cleaning mechanism could be draft of air caused by thermal gradient or a spring loaded cleaning system to clean reflective mirrors of the sensor.

According to an embodiment the processing module of the device is configured to collect data associated with the plurality of environmental parameters of the personal environment envelope from a plurality of external sources. The personal environment envelop setting module of the device is configured to learn individual's preference of the personal environmental envelope and to automatically generate the preferred settings for the individual based on the learning. When the individual moves from a first personal environment envelope to a second personal environment envelope, the personal environment envelop setting module of the device is further configured to generate adaptive comfort settings for the individual present in the second personal environment envelope based on environmental parameters of the first personal environment envelope.

Thus system, method and device disclosed would capture the personal environment of the air that the individual would seek, learn from the preferred settings the personal preferences, alert in event of deviations from the preferred settings, provide data to the backend that could through a period of time of accumulated data provide valuable health insights to the person as well as act as the database of several individuals health records to enable epidemiologists to study, analyze such data to guide policy formulations.

I claim:

1. A system for recording a personal environment envelope of an individual, the system comprises:
   a. a sensor module comprising at least one of a plurality of environmental sensors configured to sense a plurality of environmental parameters of the personal environment envelope surrounding the individual and a plurality of biological sensors to sense a plurality of biological and physiological condition of the individual;
   b. a personal environment envelop setting module configured:
      i. to define preferred settings based on input from the individual through an user interface;
      ii. to machine learn individual's preference of the personal environmental envelope; and
      iii. to automatically generate the preferred settings for the individual based on the learning by interacting and interfacing with plurality of environment setting equipment's to achieve the preferred setting for the individual;
   c. a processing module configured:
      i. to collect data from plurality of environmental sensors regarding ambient environmental conditions with reference to the geographical location of the individual;
      ii. to collect data from plurality of external sources regarding ambient environmental conditions with reference to the geographical location of the individual and the personal environmental envelope;
      iii. to dynamically process the preferred personal environment data vis-a-vis the ambient environmental conditions by concurrently mapping the personal environmental envelope of the individual with the corresponding ambient outdoor environmental conditions, when the individual moves from a first set of ambient conditions to a second new set of ambient conditions;
      iv. to process at least one of the plurality of environmental parameters sensed by the plurality of environmental sensors, the sensed biological and physiological condition of the individual and the preferred settings to generate one or more alerts, wherein the alert indicates a deviation of at least one environmental parameter from a corresponding preferred setting; and
   d. a server module configured to receive, store, analyze and machine learn from data of the plurality of environmental parameters and biological and physiological condition, sensed by the environmental sensors and biological sensors from the sensor module and the preferred settings along with ambient environmental data from plurality of individuals for epidemiology study; wherein the system tracks, records, monitors, alert for deviations of environmental parameters and enable preferred settings.

2. The system as claimed in claim 1 further comprises a communication module to receive and transmit data between various modules and to communicate alerts and interface with plurality of user devices and environment setting equipment's.

3. The system as claimed in claim 1 wherein the environment setting equipment's includes at least one of a heating ventilation and air conditioning (HVAC), air conditioner, humidifier, air filtering equipment or an actuator.

4. The system as claimed in claim 1, wherein the sensor module is further configured to perform signal conditioning for the plurality of sensors.

5. The system as claimed in claim 1, wherein the system is capable of identifying the proximity of the individual, provides an alert for variations from defined proximity.

6. The system as claimed in claim 1, wherein when the individual moves from a first set of ambient conditions to a second set of ambient conditions the personal environment envelop setting module is configured to generate thermally adaptive comfort settings for the individual present in the second ambient conditions based on environmental parameters of the first personal environment envelope and the corresponding ambient or outdoor conditions.

7. A device for recording personal environment and to enable preferred personal indoor environment the device comprises:
  a) a processor;
  b) a plurality of sensors for sensing a plurality of environmental parameters of the personal environment envelope surrounding the individual;
  c) an air flow enabling module to allow the ambient air to circulate inside the device to accurately and dynamically capture properties of air surrounding the envelope;
  d) a personal environment envelope setting module configured:
    i. to define preferred settings based on input from the individual through an user interface, wherein the user interface allows the individual to input whether the individual is allergic to environmental pollen or any other environmental related allergy;
    ii. to machine learn individual's preference of the personal environmental envelope; and
    iii. to automatically generate the preferred settings for the individual based on the learning by interacting and interfacing with plurality of environment setting equipment's to achieve the preferred setting for the individual;
  e) a processing module configured to:
    i. to collect data from plurality of sensors regarding ambient environmental conditions with reference to the geographical location of the individual;
    ii. to collect data from plurality of external sources regarding ambient environmental conditions with reference to the geographical location of the individual and the personal environmental envelope;
    iii. to dynamically provide the preferred personal environment data vis-a-vis the collected ambient environmental conditions by concurrently mapping the personal environmental envelope of the individual with the corresponding ambient outdoor environmental conditions, when the individual moves from a first set of ambient conditions to a second new set of ambient conditions, the personal environment envelope setting module is further configured to generate preferred comfort settings for the individual present in the second ambient conditions based on environmental parameters of the first personal environment envelope and the corresponding ambient outdoor conditions;
    iv. to process the plurality of environmental parameters sensed by the plurality of sensors and the preferred settings to generate one or more alerts, wherein the alert indicates a deviation of at least one environmental parameter from a corresponding preferred setting;
  f) a display unit to present the plurality of environmental parameters and alerts generated by the processing module; and g) a power supply module configured to supply power to the device.

8. The device as claimed in claim 7 further comprises a communication module configured to receive and transmit data between various modules and to communicate alerts and interface with plurality of user devices.

9. The device as claimed in claim 7, wherein the personal environment envelop setting module is further configured to interact and interface with various environment setting equipment's to achieve the preferred setting for the individual.

10. The device as claimed in claim 7, wherein the air flow enabling module employs at least one of a first louvers for air to flow into the device and a second louvers for air to move out or a mini fan to enable air circulation.

11. The device as claimed in claim 7, wherein the air flow enabling module has at least one of:
  a) a spring loaded disc that rotates to create turbulence;
  b) a heater to create a thermal gradient; or
  c) a passage to move air through a venturi effect.

12. The device as claimed in claim 7, wherein when the individual moves from a first set of ambient conditions to a second new set of ambient conditions, the personal environment envelop setting module is configured to generate adaptive comfort settings for the individual present in the second ambient conditions based on environmental parameters of the first personal environment envelope.

13. The device as claimed in claim 7, has a self-cleaning mechanism for plurality of components of the device, wherein the self-cleaning mechanism is a spring loaded cleaning system to clean reflective mirrors of the sensor.

14. The device as claimed in claim 7 has a means for wearing the device on at least one of a body, apparel or an accessory.

15. The device as claimed in claim 7, wherein the sensors are integrated in a wearable material on which the device is housed through a clip on facility.

16. The device as claimed in claim 7, wherein the power supply module has at least one of a USB port to get the device charged, a rechargeable battery, a solar cell or a wireless charging mode.

17. The device as claimed in claim 7, wherein the device further has at least one of a haptic, buzzer or light to enable alert.

* * * * *